US010338026B2

(12) United States Patent
Reinhardt et al.

(10) Patent No.: US 10,338,026 B2
(45) Date of Patent: Jul. 2, 2019

(54) METHOD AND DEVICE FOR MONITORING THE CAPABILITY OF AN EXHAUST-GAS ANALYZER PROBE TO MEASURE RICH GAS

(71) Applicant: Robert Bosch GmbH, Stuttgart (DE)

(72) Inventors: Goetz Reinhardt, Boeblingen (DE); Martin Buchholz, Bietigheim-Bissingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 373 days.

(21) Appl. No.: 15/109,318

(22) PCT Filed: Dec. 3, 2014

(86) PCT No.: PCT/EP2014/076380
§ 371 (c)(1),
(2) Date: Jun. 30, 2016

(87) PCT Pub. No.: WO2015/104102
PCT Pub. Date: Jul. 16, 2015

(65) Prior Publication Data
US 2016/0327512 A1    Nov. 10, 2016

(30) Foreign Application Priority Data
Jan. 7, 2014  (DE) .................. 10 2014 200 063

(51) Int. Cl.
*G01N 27/41*     (2006.01)
*G01N 27/417*    (2006.01)
(Continued)

(52) U.S. Cl.
CPC ....... *G01N 27/4175* (2013.01); *G01N 27/409* (2013.01); *G01N 27/4065* (2013.01);
(Continued)

(58) Field of Classification Search
CPC .......... G01N 27/4065; G01N 27/4067; G01N 27/409; G01N 27/41; G01N 27/4175; G01N 27/419; G01N 27/407; G01N 33/007
See application file for complete search history.

(56) References Cited

U.S. PATENT DOCUMENTS

2005/0252771 A1* 11/2005 Wiedenmann ..... G01N 27/4065
                                                      204/426
2012/0167656 A1*  7/2012 Verdier ............... F02D 41/1495
                                                      73/1.06

FOREIGN PATENT DOCUMENTS

CN   101573613 A   11/2009
CN   102334027 A    1/2012
(Continued)

OTHER PUBLICATIONS

English translation of International Prelimnary Report on Patentability Chapter I for Internatioal application No. PCT/EP2014/076380, published Jul. 12, 2016 (Year: 2016).*
(Continued)

*Primary Examiner* — Alexander S Noguerola
(74) *Attorney, Agent, or Firm* — Norton Rose Fulbright US LLP; Gerard Messina

(57) ABSTRACT

A method for monitoring a capability of an exhaust-gas analyzer probe in an exhaust passage of an internal combustion engine operated with lean combustion to measure rich gas. Exhaust gas is diffused in the exhaust-gas analyzer probe from the exhaust passage via a diffusion barrier into a measuring cavity of the exhaust-gas analyzer probe, and with the aid of a pump cell having an inner pump electrode and a second pump electrode, by applying a pump voltage between the electrodes, oxygen is pumped into or out of the measuring cavity according to a flowing pump current. During a lean operation mode of the internal combustion
(Continued)

engine, the pumping direction of the pump cell is reversed during a diagnostic phase and oxygen is pumped into the measuring cavity, and the capability of the exhaust-gas analyzer probe to measure rich gas is inferred from the pump current and/or the pump voltage.

6 Claims, 2 Drawing Sheets

(51) Int. Cl.
  *G01N 33/00* (2006.01)
  *G01N 27/406* (2006.01)
  *G01N 27/409* (2006.01)
  *G01N 27/419* (2006.01)
(52) U.S. Cl.
  CPC ......... *G01N 27/4067* (2013.01); *G01N 27/41* (2013.01); *G01N 27/419* (2013.01); *G01N 33/007* (2013.01)

(56) References Cited

FOREIGN PATENT DOCUMENTS

| CN | 102362175 A | 2/2012 | |
|---|---|---|---|
| CN | 102362176 A | 2/2012 | |
| DE | 102009060172 A1 | 6/2011 | |
| DE | 102010040817 A1 | 3/2012 | |
| DE | 102011005490 A1 * | 9/2012 | ........... G01N 27/407 |
| DE | 102011005490 A1 | 9/2012 | |

OTHER PUBLICATIONS

EPO computer-generated English language translation of DE 102011005490 A1 downloaded Feb. 25, 2019 (Year: 2019).*
International Search Report dated Feb. 25, 2015, of the corresponding International Application PCT/EP2014/076380 filed on Dec. 3, 2014, 2 pages.

* cited by examiner

METHOD AND DEVICE FOR MONITORING THE CAPABILITY OF AN EXHAUST-GAS ANALYZER PROBE TO MEASURE RICH GAS

FIELD

The present invention relates to a method for monitoring a capability of an exhaust-gas analyzer probe in an exhaust passage of an internal combustion engine operated with lean combustion to measure rich gas, in which exhaust gas is diffused in the exhaust-gas analyzer probe from the exhaust passage via a diffusion barrier into a measuring cavity of the exhaust-gas analyzer probe, and with the aid of a pump cell having an inner pump electrode and a second pump electrode, by applying a pump voltage between the electrodes, oxygen is pumped into or out of the measuring cavity commensurate with a flowing pump current.

The present invention also relates to a device for monitoring a capability of an exhaust-gas analyzer probe in an exhaust passage of an internal combustion engine operated with lean combustion to measure rich gas, a measuring cavity of the exhaust-gas analyzer probe being connected via a diffusion barrier to the exhaust passage, a pump cell having an inner pump electrode and a second pump electrode being provided to pump oxygen into or out of the measuring cavity, a positive pump current being provided between the electrodes to pump oxygen out of the measuring cavity and a negative pump current being provided between the electrodes to pump oxygen in, and a control unit being assigned to the exhaust-gas analyzer probe.

BACKGROUND INFORMATION

Exhaust-gas analyzer probes are used, for example, in the form of lambda oxygen sensors in the exhaust passage of internal combustion engines to determine the composition of an air-fuel mixture fed to the internal combustion engine. According to statutory regulations, the exhaust-gas analyzer probes must be checked during operation for correct functioning, what is referred to as "measuring capability." To that end, a gaseous mixture of known composition may be fed to the exhaust-gas analyzer probe, and the output signal of the exhaust-gas analyzer probe may be evaluated. When checking a lambda oxygen sensor for correct functioning in the case of a "rich" air-fuel ratio with a lambda value <1, the checking of what is referred to as the "rich gas measuring capability," such a mixture would thus have to be supplied to the lambda oxygen sensor. Particularly for diesel engines which are operated in the range of a lean exhaust gas during normal operation, operation with a rich mixture for a diagnosis leads to increased emission of pollutants as well as additional fuel consumption, and is therefore preferably avoided. Other possibilities for making a rich gas composition available at the lambda oxygen sensor without intervening in the engine operation are not feasible for multiple reasons.

However, a reliable diagnosis in another way is also fraught with disadvantages. The pump current of the lambda oxygen sensor is used to determine the lambda value. The pump current is positive in the case of lean exhaust gas and negative in the case of rich exhaust gas. The transport processes within the lambda oxygen sensor for lean exhaust gas and rich exhaust gas differ considerably in terms of the direction of current flow, electrode reaction and gases at the electrodes. For a realistic diagnosis, these conditions must therefore be made available, in so far as necessary for the diagnosis.

Exhaust-gas analyzer probes may be realized as broadband lambda sensors, lambda voltage-jump sensors, two-cell broadband lambda sensors or single-cell limit-current sensors, but also, for example, as $NO_x$-sensors.

German Patent Application No. DE 10 2011 005 490 A1 describes a method for operating a sensor element to detect at least one property of a gas in a measuring-gas compartment, the sensor element including at least one pump cell having at least two electrodes and at least one solid electrolyte connecting the electrodes, at least one first electrode of the pump cell being able to be acted upon with gas from the measuring-gas compartment, at least one second electrode of the pump cell being connected to at least one reference channel, the method being used to check whether a pump current through the pump cell is limited by an impingement of gas on the first electrode, or whether the pump current through the reference channel is limited. The description alludes to the possibility of a pump-voltage reversal for diagnostic purposes. However, the diagnosis of the capability of an exhaust-gas analyzer probe to measure rich gas is not discussed in the document.

German Patent Application No. DE 10 2010 040 817 A1 describes a method for the adjustment of a sensor element to detect at least one property of a gas in a measuring-gas compartment, especially to determine one constituent of a gas component, the sensor element having at least two cells, each having at least two electrodes and at least one solid electrolyte connecting the electrodes, at least one first electrode being part of both cells, the first electrode being able to be acted upon via at least one diffusion barrier with gas from the measuring-gas compartment, the cells including at least one first cell and at least one second cell, at least one gas component of the gas pumped from the first electrode through a second cell being at least partially returnable via the diffusion barrier to the first electrode, a first pump current through the first cell being measured, a second pump current through the second cell being measured, and at least one property of the diffusion barrier being inferred from the first pump current and the second pump current. The document describes that the characteristic curve of a broadband lambda sensor may be adjusted during or after production or even during field operation, e.g., in an overrun condition of a diesel engine. In doing so, suitable diagnostic processes and/or regeneration processes may be carried out, e.g., with the aid of a pump-current reversal and/or pumping up of the electrode cavity. A method for diagnosing the capability of the lambda oxygen sensor to measure rich gas is not described.

German Patent Application DE 10 2009 060 172 A1 describes a method for diagnosing a dynamic response of an exhaust-gas sensor, by which a property of an exhaust-gas flow is able to be characterized, the exhaust-gas sensor having a measuring control loop, and the property of the exhaust-gas flow being able to be characterized with the aid of an actuating signal of the measuring control loop, the method including:
  producing a change in the actuating signal,
  ascertaining a reaction of a measuring signal of the measuring control loop to the change, and
  judging the dynamic response of the exhaust-gas sensor with the aid of the reaction.

The document alludes to the possibility that instead of a mixture composition of the exhaust-gas mass flow, by switching off and/or switching over the regulator or its actuating signal, which may occur in an integrated circuit of the regulator or an engine control unit of a combustion engine producing the exhaust-gas flow, for example, the oxygen content in the reference cell may be changed. In this instance, the possibility for diagnosing the capability of the exhaust-gas sensor to measure rich gas for engines operated with lean combustion is not described.

SUMMARY

An object of the present invention is to provide a method and a device which make it possible to check the correct functioning of an exhaust-gas analyzer probe and an associated measuring circuit to determine the composition of a rich exhaust-gas mixture, without applying rich exhaust gas to the exhaust-gas analyzer probe.

An object of the present invention pertaining to the method is achieved in that during a lean operation mode of the internal combustion engine, the pumping direction of the pump cell is reversed during a diagnostic phase and oxygen is pumped into the measuring cavity, and the capability of the exhaust-gas analyzer probe to measure rich gas is inferred from the pump current and/or the pump voltage.

In this context, an intact exhaust-gas analyzer probe or intact assigned probe electronics may be inferred if a pump-current direction reversed for the lean operation mode is able to be set.

During normal measuring operation for an internal combustion engine operated with lean combustion, e.g., in the case of a diesel engine, oxygen diffuses out of the exhaust gas through the diffusion barrier into the measuring cavity of the exhaust-gas analyzer probe. According to the operating strategy, a lambda of 1, for example, prevails in the measuring cavity. The oxygen diffusing into the measuring cavity is removed by the pump cell with a positive pump current.

To diagnose the rich-gas measuring capability, the pump voltage is modified in such a way that a negative pump current must ensue. As a result, oxygen is pumped into the measuring cavity. The measured pump current is evaluated for the diagnosis. If no negative pump current occurs, a defect exists in the exhaust-gas analyzer probe or the assigned measuring circuit.

The method makes it possible to check the capability of the exhaust-gas analyzer probe and the assigned probe electronics to measure rich gas, without the necessity of feeding rich exhaust gas to the exhaust-gas analyzer probe. Increased fuel consumption as well as increased emission of pollutants may thus be avoided during the diagnosis. The monitoring may therefore be carried out often enough to comply with the standards of the "in use monitor performance ratio" (IUMPR), for example.

A precise evaluation of the capability of the exhaust-gas analyzer probe to measure rich gas may be achieved by taking the pump voltage or the pump current or the time characteristic of the pump voltage or the time characteristic of the pump current upon reversed pump-current direction or the composition of the exhaust gas into account, in each instance considered by itself or in combination of the characteristic quantities, to evaluate the capability of the exhaust-gas analyzer probe to measure rich gas.

According to a further variant of the present invention, a predefined reversed pump current may be set with the aid of a regulator, and the pump voltage necessary for that purpose may be evaluated to assess the capability of the exhaust-gas analyzer probe to measure rich gas. The composition of the exhaust gas at the exhaust-gas analyzer probe may be taken into account here, as well.

A further option for diagnosing the exhaust-gas analyzer probe is obtained from the possibility that, subsequent to the diagnostic phase, in a following measuring operation, the pumping direction of the pump cell is reversed again and oxygen is pumped out of the measuring cavity, and that an oxygenation in the measuring cavity and/or a performance of the pump cell and/or a functional reserve of the exhaust-gas analyzer probe available for the lean operation mode is/are inferred from a resulting maximum pump current.

After returning from the diagnostic phase to the measuring operation, the signal of the exhaust-gas analyzer probe is invalid for a brief time for determining the exhaust-gas composition, until a lambda of approximately 1 has set in again in the measuring cavity. To avoid a faulty measurement, it may therefore be provided that after a diagnostic phase, in the regular measuring operation, the output signal of the exhaust-gas analyzer probe is evaluated after a predetermined waiting time.

The object of the present invention pertaining to the device is achieved in that, in the control unit, a circuit or a program run is provided for reversing the pumping direction of the pump cell during a lean operation mode of the internal combustion engine and during a diagnostic phase of the exhaust-gas analyzer probe, and that the control unit includes a circuit or a program run for diagnosing a correct rich-gas measuring capability upon occurrence of negative current values during the diagnostic phase. Thus, the device permits the implementation of the method described.

According to one especially preferred embodiment variant of the present invention, the exhaust-gas analyzer probe may be realized as a broadband lambda sensor or as a nitrogen oxide sensor. In both exhaust-gas analyzer probes, the concentration of the respective exhaust-gas component, thus, oxygen or nitrogen oxide ($NO_x$), is ascertained on the basis of a developing pump current.

In a further variant of the present invention, the exhaust-gas analyzer probe may be realized as a single-cell limit-current probe with integrated oxygen storage.

BRIEF DESCRIPTION OF THE DRAWINGS

The present invention is explained in greater detail below based on an exemplary embodiment shown in the figures.

DETAILED DESCRIPTION OF EXAMPLE EMBODIMENTS

Figure 1:
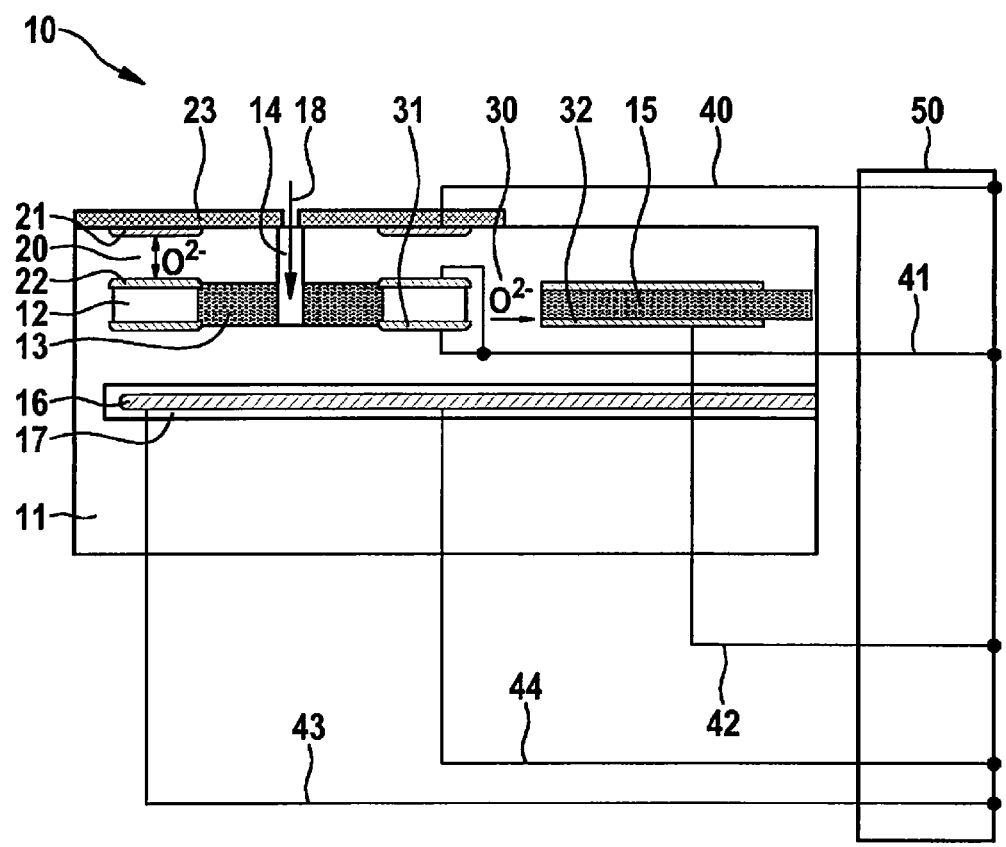
FIG. 1 shows a schematic representation of a sensor element of a two-cell broadband lambda sensor.

FIG. 1 shows a schematic representation of a sensor element 10 of a planar, two-cell broadband lambda sensor for determining a lambda value of an exhaust gas 18, having a plug-connector housing 50. Sensor element 10 is constructed generally of a solid-state electrolyte 11. It includes a pump cell 20, a concentration cell 30 and a heating element 16. Solid-state electrolyte 11 is shown in the drawing as a homogenous body made of oxygen-ion-conducting zirconium dioxide, however, it may be made up of a plurality of solid-electrolyte layers.

Pump cell 20 is made up of an inner pump electrode 22 disposed in a measuring cavity 12 and an outer second pump electrode 21. Outer pump electrode 21, covered by a protective layer 23, is exposed to exhaust gas 18 of an internal combustion engine (not shown). Outer pump electrode 21 and inner pump electrode 22 are disposed annularly around a diffusion channel 14. Diffusion channel 14 delivers exhaust gas 18 via a diffusion barrier 13 to measuring cavity 12.

On the side of measuring cavity 12 opposite inner pump electrode 22, a measuring electrode 31 is disposed. Measuring electrode 31, together with a reference electrode 32 located in a reference channel 15 and solid-state electrolyte 11 situated in between, form concentration cell 30. Reference channel 15 is filled with an air-permeable material, and is open to the exterior air as reference gas. In the case of a pumped reference, reference channel 15 may also be completely or largely closed and filled with zirconium oxide, for example.

Heating element 16 is separated electrically from solid-state electrolyte 11 by an insulating material 17.

Outer pump electrode 21 is connected to plug-connector housing 50 via a connection OPE 40. Inner pump electrode 22 and measuring electrode 31 are connected in parallel and are connected via one common connection IPE 41 to plug-connector housing 50. Reference electrode 32 is connected via a connection RE 42, and heating element 16 is connected via a first heating-element connection 43 and a second heating-element connection 44 to plug-connector housing 50. The exhaust-gas analyzer probe is electrically connected via plug-connector housing 50 to probe electronics, e.g., a control unit, not shown.

During operation of the broadband lambda sensor, exhaust gas 18 diffuses via diffusion channel 14 and diffusion barrier 13 into measuring cavity 12. The lambda value in measuring cavity 12 is determined via concentration cell 30 by measuring the Nernst voltage between measuring electrode 31 and reference electrode 32. In so doing, concentration cell 30 makes it possible to determine the lambda in a narrow measuring window around lambda=1. By applying a suitably polarized voltage between second and inner pump electrodes 21, 22, oxygen ions are able to be pumped through solid-state electrolyte 11 from exhaust gas 18 into measuring cavity 12 or out of measuring cavity 12 to exhaust gas 18.

By a suitable closed-loop control of the pump current flowing between pump electrodes 21, 22, and therefore the exchange of oxygen ions between measuring cavity 12 and exhaust gas 18, the lambda in measuring cavity 12 is regulated to a value of 1. The lambda value in measuring cavity 12 is monitored by concentration cell 30. The value of the pump current necessary to that end is a function of the oxygen concentration, and therefore of the lambda value of exhaust gas 18 to be determined, as well as of the diffusion properties of diffusion barrier 13.

If such a two-cell broadband lambda sensor is utilized in exhaust gas 18 of a diesel engine operated with lean combustion, then oxygen diffuses out of exhaust gas 18 via diffusion channel 14 and diffusion barrier 13 into measuring cavity 12. The oxygen is pumped out of measuring cavity 12 into exhaust gas 18 by a voltage applied suitably between inner pump electrode 22 and outer second pump electrode 21, and the consequent positive pump current.

The correct functioning of the broadband lambda sensor is monitored as part of an on-board diagnostic. To that end, the capability of the broadband lambda sensor to measure rich gas must also be verified. In the case of a diesel engine, for that purpose, a rich exhaust gas 18 would have to be adjusted by a suitable intervention in the engine operation, which, however, is disadvantageous because of the negative influence on the emission of pollutants and the fuel consumption. Therefore, according to the present invention, during a diagnostic phase, a negative pump current is set with the aid of a controlled change of the pump voltage. In this case, oxygen at inner pump electrode 22 is released into measuring cavity 12, provided a negative pump current is actually flowing. Consequently, a gas with a lambda greater than 1 forms in measuring cavity 12.

The measured pump current is evaluated for the diagnosis. If no negative pump current occurs, a defect exists. Moreover, taking into account the gas composition at sensor element 10, the pump voltage which is set at pump cell 20 may also be evaluated. In a further expansion level, a regulator is provided which attempts to set a predefined negative pump current. In this case, the pump voltage necessary for this may be evaluated, likewise in due consideration of the composition of exhaust gas 18 present.

The method makes it possible, for example, to recognize a manipulation of the broadband lambda sensor and the connected probe electronics, in which a diode was introduced into the pump-cell circuit to prevent a negative pump current.

After the diagnostic phase, at the beginning of the following measuring operation, the signal of the broadband lambda sensor is still invalid for a brief time for determining the composition of exhaust gas 18, until a lambda of 1 has set in again in measuring cavity 12.

In a further expansion level of the present invention, the increased pump current, which ensues upon the return to regular measuring operation owing to the evacuation of measuring cavity 12, is evaluated. The peak of the pump current is a measure both for the oxygenation in measuring cavity 12 and for the performance of pump cell 20. In addition, it is suited for diagnosing the functional reserve available for the lean operation mode of the broadband lambda sensor.

Figure 2:
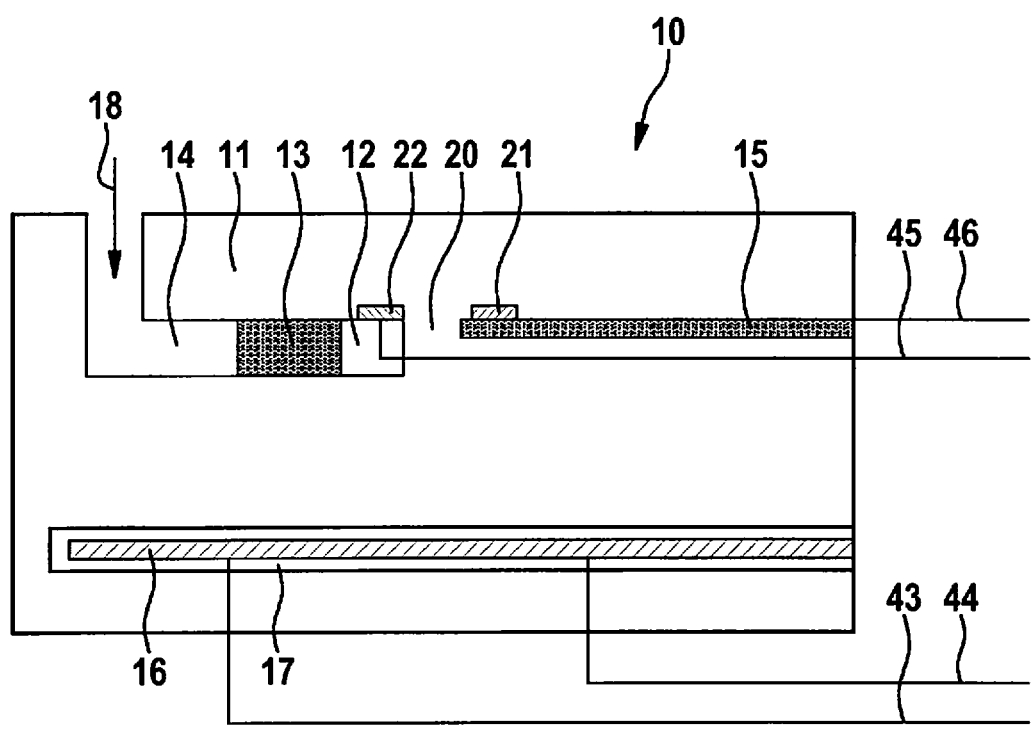
FIG. 2 shows the sensor element of a single-cell exhaust-gas analyzer probe.

FIG. 2 shows sensor element 10 of a single-cell exhaust-gas analyzer probe having a solid electrolyte 11 as base element and a diffusion channel 14 that is open toward an exhaust passage of an internal combustion engine (not shown). The exhaust-gas analyzer probe is used as lambda oxygen sensor for determining the composition of the air-fuel mixture fed to the internal combustion engine. For example, solid-state electrolyte 11 is produced from yttrium-stabilized zirconium dioxide, which is ion-conducting at operating temperature, and together with an appropriate placement of electrodes and gas feeds, is suited to determine a concentration of certain components of a gas composition. Exhaust gas 18 enters via diffusion channel 14 through a diffusion barrier 13 into a measuring cavity 12. Diffusion barrier 13 is a porous element which at least largely prevents gas from flowing back out of diffusion channel 14 into measuring cavity 12 or in the reverse direction, and permits only a diffusion transport. In measuring cavity 12, a portion of the wall of solid-state electrolyte 11 is covered with a first inner pump electrode 22 that is connected via a second lead 46 to the outside. In addition, solid electrolyte 11 has a reference-gas channel 15 that is filled with a porous gas-permeable medium, and whose wall is covered partially with a second pump electrode 21. Second pump electrode 21 is connected to the outside via a first lead 45. Reference-gas channel 15 is also referred to as exhaust-air duct (EAD), second pump electrode 21 also as exhaust-air electrode (EAE). In the exemplary embodiment shown, inner pump electrode 22 and second pump electrode 21 are disposed inside the base element realized as a layer construction.

Inner pump electrode 22, second pump electrode 21 and the part of solid-state electrolyte 11 lying in between together form a pump cell 20.

In addition, in the exemplary embodiment shown, the exhaust-gas analyzer probe includes a heating element 16 having an insulating material 17 that surrounds heating element 16 and, at operating temperature, prevents an electrical contact with other components in the exhaust-gas analyzer probe. Heating element 16 is supplied with operating voltage via a first heating-element connection 43 and a second heating-element connection 44. The operating voltage is regulated by an assigned control or probe electronics in such a way that a predefined internal resistance of pump cell 20 ensues. In the control or probe electronics, the electric voltages at inner pump electrode 22 and second pump electrode 21 are also predefined or determined, and the currents in the first and second leads 45, 46 are predefined or determined. As example of a realization, inner pump electrode 22, to which exhaust gas 18 is applied, is connected to a virtual ground of the control. This virtual ground connects first inner pump electrode 22 to a constant electrode potential relative to an electric ground. Second pump electrode 17 or the exhaust-air electrode, on the other hand, is at a variable potential. Via a pump-voltage source, a pump current $l_P$ through pump cell 20 is determined with the aid of a current-measuring device, e.g., with the aid of a measuring resistor. When working with customary circuits, this is accomplished in such a way that a pump voltage $U_P$ of the pump-voltage source is regulated via an infeed at a non-inverting input of an operational amplifier, so as to set a higher pump voltage of 900 mV in a measurement in connection with air, however to set a smaller pump voltage $U_P$ of 200 mV in the case of rich gas. A Nernst voltage $U_N$, which is a function of the composition of the exhaust gas, ensues between inner pump electrode 22 and second pump electrode 21.

Like in the case of the two-cell broadband lambda sensor shown in FIG. 1, in response to a lean exhaust gas 18, oxygen from exhaust gas 18 diffuses via diffusion channel 14 and diffusion barrier 13 into measuring cavity 12 when working with the single-cell exhaust-gas analyzer probe shown here, as well. The oxygen is pumped out of measuring cavity 12 into reference channel 15 by a voltage applied suitably between inner pump electrode 22 and second pump electrode 21, and the consequent positive pump current.

According to the present invention, to diagnose the capability of the exhaust-gas analyzer probe to measure rich gas while exhaust gas 18 is still lean, a pump voltage $U_P$ is applied temporarily between inner pump electrode 22 and second pump electrode 21, which yields a negative pump current. Oxygen is thereby pumped out of reference-gas channel 15 into measuring cavity 12. During this diagnostic phase, the output signal of the exhaust-gas analyzer probe is not suited to determine the lambda value.

As already described in connection with FIG. 1, the measured pump current is evaluated for the diagnosis. If no negative pump current occurs, there is a defect. In this context, the same evaluation methods may be utilized when using the single-cell exhaust-gas analyzer probe as when using the two-cell broadband lambda sensor described in FIG. 1.

The diagnosis is also possible during digital discontinuous operation of the electrochemical cell with a pulsating pump current.

What is claimed is:

1. A method for monitoring a capability of an exhaust-gas analyzer probe in an exhaust passage of an internal combustion engine operated with lean combustion to measure rich gas, in which exhaust gas is diffused in the exhaust-gas analyzer probe from the exhaust passage via a diffusion barrier into a measuring cavity of the exhaust-gas analyzer probe, and with the aid of a pump cell having an inner pump electrode and a second pump electrode, by applying a pump voltage between the electrodes, oxygen is pumped into or out of the measuring cavity according to a flowing pump current, the method comprising:

during a lean operation mode of the internal combustion engine, in a diagnostic phase, reversing a pumping direction of the pump cell and pumping oxygen into the measuring cavity; and inferring a capability of the exhaust-gas analyzer probe to measure rich gas from one of: i) the pump current, and ii) the pump voltage.

2. The method as recited in claim 1, wherein an intact exhaust-gas analyzer probe or intact assigned probe electronics is inferred if a pump-current direction reversed for the lean operation mode is able to be set.

3. The method as recited in claim 1, to evaluate the capability of the exhaust-gas analyzer probe to measure rich gas, at least one of: i) the pump voltage, ii) the pump current, iii) a time characteristic of the pump voltage, iv) a time characteristic of the pump current upon reversed pump-current direction, and v) a composition of the exhaust gas, is taken into account.

4. The method as recited in claim 1, wherein a predefined reversed pump current is set with the aid of a regulator, and the pump voltage necessary for that purpose is evaluated to assess the capability of the exhaust-gas analyzer probe to measure rich gas.

5. The method as recited claim 1, wherein subsequent to the diagnostic phase, in a following measuring operation, the pumping direction of the pump cell is again reversed and oxygen is pumped out of the measuring cavity, and at least one of: i) an oxygenation in the measuring cavity, ii) a performance of the pump cell, and iii) a functional reserve of the exhaust-gas analyzer probe available for the lean operation mode is inferred from a resulting maximum pump current.

6. The method as recited in claim 1, wherein after a diagnostic phase, during a regular measuring operation, an output signal of the exhaust-gas analyzer probe is evaluated after a predefined waiting time.

\* \* \* \* \*